United States Patent
Nichols et al.

(10) Patent No.: US 9,998,667 B2
(45) Date of Patent: Jun. 12, 2018

(54) ROTATION STABILIZATION

(71) Applicant: SmugMug, Inc., Mountain View, CA (US)

(72) Inventors: Samuel Nichols, Mountain View, CA (US); Don Macaskill, Los Altos, CA (US)

(73) Assignee: SmugMug, Inc., Mountain View, CA (US)

( * ) Notice: Subject to any disclaimer, the term of this patent is extended or adjusted under 35 U.S.C. 154(b) by 0 days. days.

(21) Appl. No.: 15/367,034

(22) Filed: Dec. 1, 2016

(65) Prior Publication Data
US 2017/0085797 A1    Mar. 23, 2017

Related U.S. Application Data

(63) Continuation of application No. 14/423,207, filed as application No. PCT/US2013/056141 on Aug. 22, 2013, now Pat. No. 9,843,729.

(60) Provisional application No. 61/692,559, filed on Aug. 23, 2012.

(51) Int. Cl.
*H04N 5/232* (2006.01)
*H04N 5/262* (2006.01)
(Continued)

(52) U.S. Cl.
CPC ....... *H04N 5/23267* (2013.01); *C07D 409/12* (2013.01); *H04N 1/2112* (2013.01);
(Continued)

(58) Field of Classification Search
CPC ........... H04N 5/23267; H04N 5/23258; H04N 1/3877; G06T 2207/20132; G06T 2210/22
See application file for complete search history.

(56) References Cited

U.S. PATENT DOCUMENTS 5,900,909 A * 5/1999 Parulski ............... H04N 1/2112
348/231.6
2002/0028071 A1  3/2002 Molgaard
(Continued)

FOREIGN PATENT DOCUMENTS

| EP | 1071285 A1 | 1/2001 |
| EP | 2518993 A1 | 10/2012 |
| EP | 2621160 A1 | 7/2013 |
| WO | 2011077788 A1 | 6/2011 |
| WO | 2012039311 A1 | 3/2012 |

OTHER PUBLICATIONS

International Search Report and Written Opinion, PCT/US2013/056141 , dated Oct. 10, 2013.
(Continued)

*Primary Examiner* — Ahmed A Berhan
(74) *Attorney, Agent, or Firm* — Patterson + Sheridan, LLP

(57) ABSTRACT

Embodiments of the present invention include methods and apparatus for the rotational stabilization of images and video. Rotational stabilization of images includes determining an amount of degrees of cant or tilt of an image capturing device, and capturing an image. The captured image is rotated an angular distance equal to the amount of degrees of tilt of the image capturing device. The rotated image is then cropped. The determining, rotating, and cropping are generally performed automatically by the image capturing device without user action at the time of capturing the image.

20 Claims, 9 Drawing Sheets

(51) Int. Cl.
   *H04N 1/21*      (2006.01)
   *C07D 409/12*    (2006.01)
   *G06T 3/60*      (2006.01)

(52) U.S. Cl.
   CPC ..... *H04N 5/23229* (2013.01); *H04N 5/23258* (2013.01); *H04N 5/23293* (2013.01); *H04N 5/23296* (2013.01); *H04N 5/2628* (2013.01); *G06T 3/60* (2013.01); *G06T 2210/22* (2013.01)

(56) References Cited

U.S. PATENT DOCUMENTS

| | | | |
|---|---|---|---|
| 2003/0152291 A1* | 8/2003 | Cheatle | G06K 9/32 382/296 |
| 2005/0093891 A1 | 5/2005 | Cooper | |
| 2011/0193982 A1 | 8/2011 | Kook et al. | |
| 2011/0194789 A1 | 8/2011 | Konno | |
| 2012/0182240 A1 | 7/2012 | Urushihata | |
| 2012/0229380 A1* | 9/2012 | Silvester | G06F 1/1626 345/158 |

OTHER PUBLICATIONS

Office Action for U.S. Appl. No. 14/423,207 dated Feb. 11, 2016.
Final Office Action for U.S. Appl. No. 14/423,207 dated Aug. 30, 2016.

\* cited by examiner

ROTATION STABILIZATION

CROSS-REFERENCE TO RELATED APPLICATIONS

This application is a continuation of and claims benefit to U.S. patent application Ser. No. 14/423,207, filed Feb. 23, 2015, which was the National Stage of International Application No. PCT/US2013/056141, filed Aug. 22, 2013, which claims benefit of U.S. Provisional Patent Application No. 61/692,559, filed Aug. 23, 2012, all of which are hereby incorporated by reference in their entirety.

BACKGROUND OF THE INVENTION

Field of the Invention

Embodiments of the invention generally relate to digital photography.

Description of the Related Art

Digital photography is becoming increasingly more popular. Many digital photographs are taken "off-hand" or without the use of tripods or other mounting devices. Photographs taken off-hand often have at least some degree of tilt or rotation in the image, due to a photographer's inability to hold to a digital camera completely level while taking the photograph. Removal of the cant or tilt in the image requires time consuming post-processing with expensive editing software. Additionally, because the images need to be edited after the fact, the images are not immediately available for sharing, such as on social media.

Therefore, there is a need for a method and apparatus which corrects image rotation at the time the image is captured.

SUMMARY OF THE INVENTION

Embodiments of the present invention include methods and apparatus for the rotational stabilization of images and video. Rotational stabilization of images includes determining an amount of degree of cant or tilt of an image capturing device, and capturing an image. The captured image is rotated an angular distance equal to the amount of degrees of tilt of the image capturing device. The rotated image is then cropped. The determining, rotating, and cropping are generally performed automatically by the image capturing device without user action at the time of capturing the image.

In one embodiment, a method of processing a digital image comprises receiving an instruction to capture an image, and in response to receiving the instruction, determining an angle of cant of an image capturing device. An image is then captured, and in response to capturing the image, the captured image is rotated a number of degrees equal to the angle of cant to form a rotated image. In response to rotating the captured image, the rotated image is cropped.

In another embodiment, a non-transitory computer readable medium comprises a sequence of instructions for pre-recording a video. When the instructions are executed by a processing unit of a system, the instructions cause the system to receive an instruction to capture an image, and in response to receiving the instruction, determine an angle of cant of an image capturing device. The image is then captured, and in response to capturing the image, the captured image is rotated a number of degrees equal to the angle of cant to form a rotated image. In response to rotating the captured image, the rotated image is cropped.

In another embodiment, a system comprises a camera, a processing unit, one or more accelerometers, and a non-transitory computer readable medium. The non-transitory computer readable medium has a sequence of instructions for pre-recording a video, which when executed by the processing unit, causes the system to receive an instruction to capture an image. In response to receiving the instruction, an angle of cant of an image capturing device is determine. The image is then captured. In response to capturing the image, the captured image is rotated a number of degrees equal to the angle of cant to form a rotated image. In response to rotating the captured image, the rotated image is cropped.

In another embodiment, a method of recording video comprises receiving an instruction to capture a video, and in response to receiving the instruction, capturing the video in a first orientation. A change from the first orientation to a second orientation is then detected, and the video is captured in the second orientation which is different than the first orientation. An instruction to stop capturing the video is then received, and in response to receiving the instruction to stop capturing the video, the captured video is processed. Processing the captured video includes orienting the video in the second orientation.

In another embodiment, a non-transitory computer readable medium includes a sequence of instructions for recording a video. When the instructions are executed by a processing unit of a system, the instructions cause the system to receive an instruction to capture a video. In response to receiving the instruction, the video is captured in a first orientation. A change from the first orientation to a second orientation is then detected, and the video is captured in the second orientation which is different than the first orientation. An instruction to stop capturing the video is then received, and in response to receiving the instruction to stop capturing the video, the captured video is processed. Processing the captured video comprises orienting the video captured in the first orientation to the second orientation.

In another embodiment, a system comprises a camera, a processing unit, one or more accelerometers, and a non-transitory computer readable medium. The non-transitory computer readable medium has a sequence of instructions for recording a video, which when executed by a processing unit of a system, causes the system to receive an instruction to capture a video. In response to receiving the instruction, the video is captured in a first orientation. The video is then captured in a second orientation different than the first orientation. An instruction to stop capturing the video is received, and in response to receiving the instruction to stop capturing the video, the captured video is processed. Processing the captured video comprises orienting the video captured in the first orientation to the second orientation.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Embodiments of the present invention include methods and apparatus for the rotational stabilization of images and video. Rotational stabilization of images includes determining an amount of degree of cant or tilt of an image capturing device, and capturing an image. The captured image is rotated an angular distance equal to the amount of degrees of tilt of the image capturing device. The rotated image is then cropped. The determining, rotating, and cropping are generally performed automatically by the image capturing device without user action at the time of capturing the image.

Figure 1:
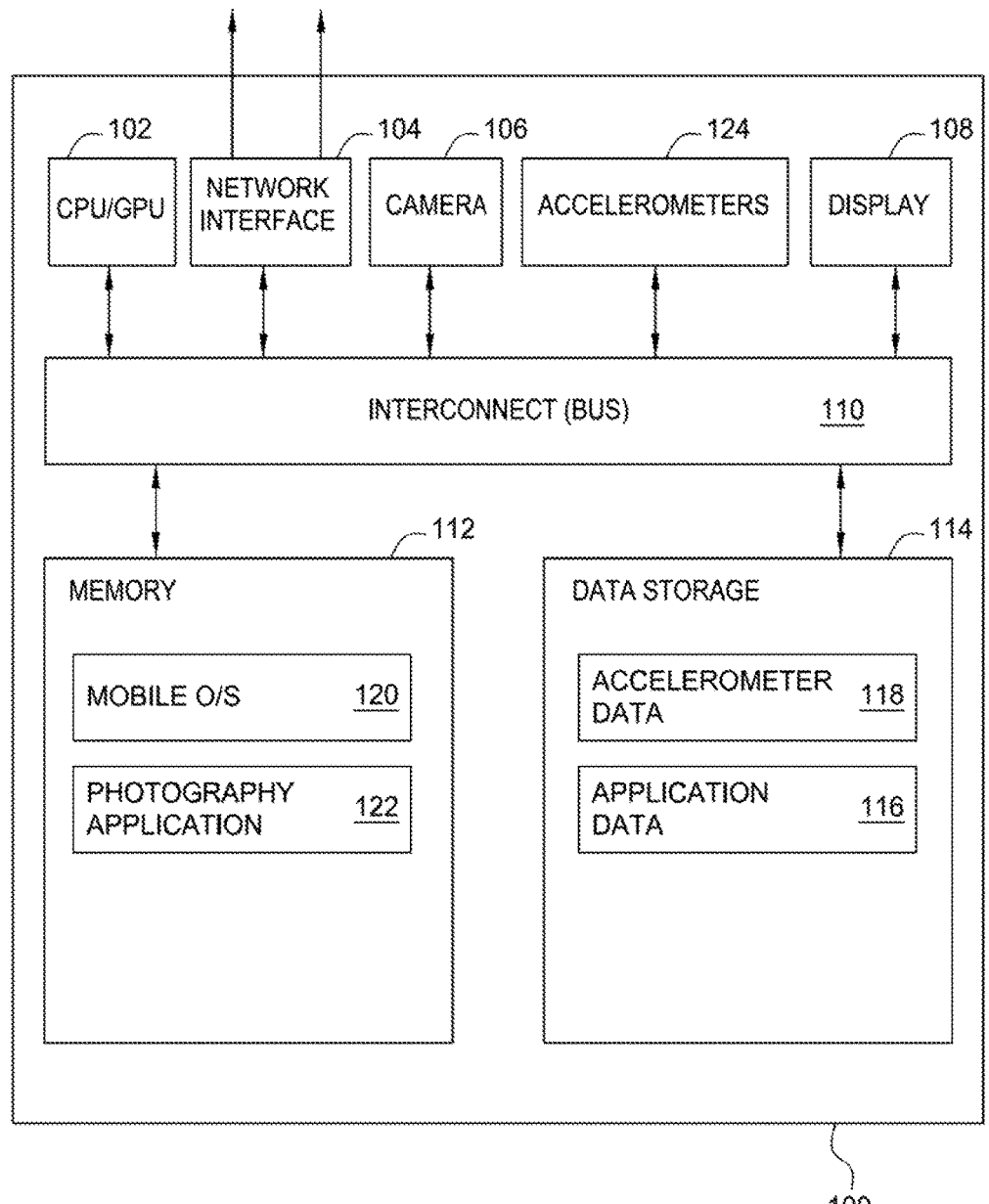
FIG. 1 illustrates an example of a system according to one embodiment of the invention.

FIG. 1 illustrates an example of a system 100 according to one embodiment of the invention. In this example, the system 100 is presumed to be a smart phone having a camera 106 and one or more accelerometers 124. Of course, embodiments of the invention may be adapted for use with a variety of image capturing devices, such as tablet computers, digital cameras and other computing devices having a camera 106 and one or more accelerometers 124.

As shown, the system 100 includes, without limitation, a central processing unit and graphics processing unit (CPU/GPU) 102, optional network interfaces 104, an interconnect 110, a memory 112, and a data storage 114. The system 100 may also include a display 108, such as a touch-sensitive display, and other hardware components used to determine an orientation (or position) of the device (e.g., a magnetometer used to track a compass-facing direction of display 108). Each accelerometer 124 may be configured to measure the acceleration of the system 100 (relative to freefall) in a distinct dimension (e.g., X, Y, and Z dimensions), and may be adapted to determine the orientation of the system 100.

The CPU/GPU 102 retrieves and executes programming instructions stored in the memory 112. Similarly, the CPU/GPU 102 stores and retrieves application data, such as the application data 116, residing in the data storage 114. The interconnect 110 is used to transmit programming instructions and application data 116 between the CPU/GPU 102, the data storage 114, the network interfaces 104, and the memory 112. The CPU/GPU 102 is included to be representative of a single CPU, multiple CPUs, a single CPU having multiple processing cores, and the like. The memory 112 is generally included to be representative of a random access memory. The data storage 114, such as a hard disk drive or flash memory storage drive, may store non-volatile data. The accelerometers 124 provide components that measure proper acceleration of the system 100, e.g., acceleration of the system 100 relative to freefall. In one embodiment, the accelerometers 124 may be configured to detect magnitude and/or direction of the acceleration of the system 100 as a vector quantity at a specified rate, e.g., 100 Hz. The camera 106 may be a CCD device configured to capture still-images and video which is stored in the data storage 114, for example, as application data 116. The application data 116 may be inclusive of both video data and still-image photography data.

Illustratively, the memory 112 includes a mobile operating system (O/S) 120 and a photography application 122. The data storage 114 includes application data 116 and accelerometer data 118. The mobile O/S 120 provides software configured to control the execution of application programs on the system 100.

The photography application 122 may be adapted to capture photographs and video images, and save the associated images and videos to the data storage 114. The photography application 122 may also be adapted to edit the captured photographs and videos. In one example, the photography application 122 edits the images and videos without user input, including rotating and cropping the images and videos. Stated another way, post-capture processing of the captured images and videos is performed automatically by the photography application 122 at the time the images and videos are captured. In such an embodiment, the edited images and videos may be stored in the data storage 114 alone or in combination with the unedited images and videos.

It will be appreciated that the system 100 shown herein is illustrative and that variations and modifications are contemplated. The connection topology, including the number and arrangement of bridges, may be modified as desired. For instance, in some embodiments, the memory 112 may be connected to the CPU/GPU 102 directly rather than through a bridge. Additionally, it is contemplated that any number of add-in cards or peripheral devices may be supported.

Figure 2:
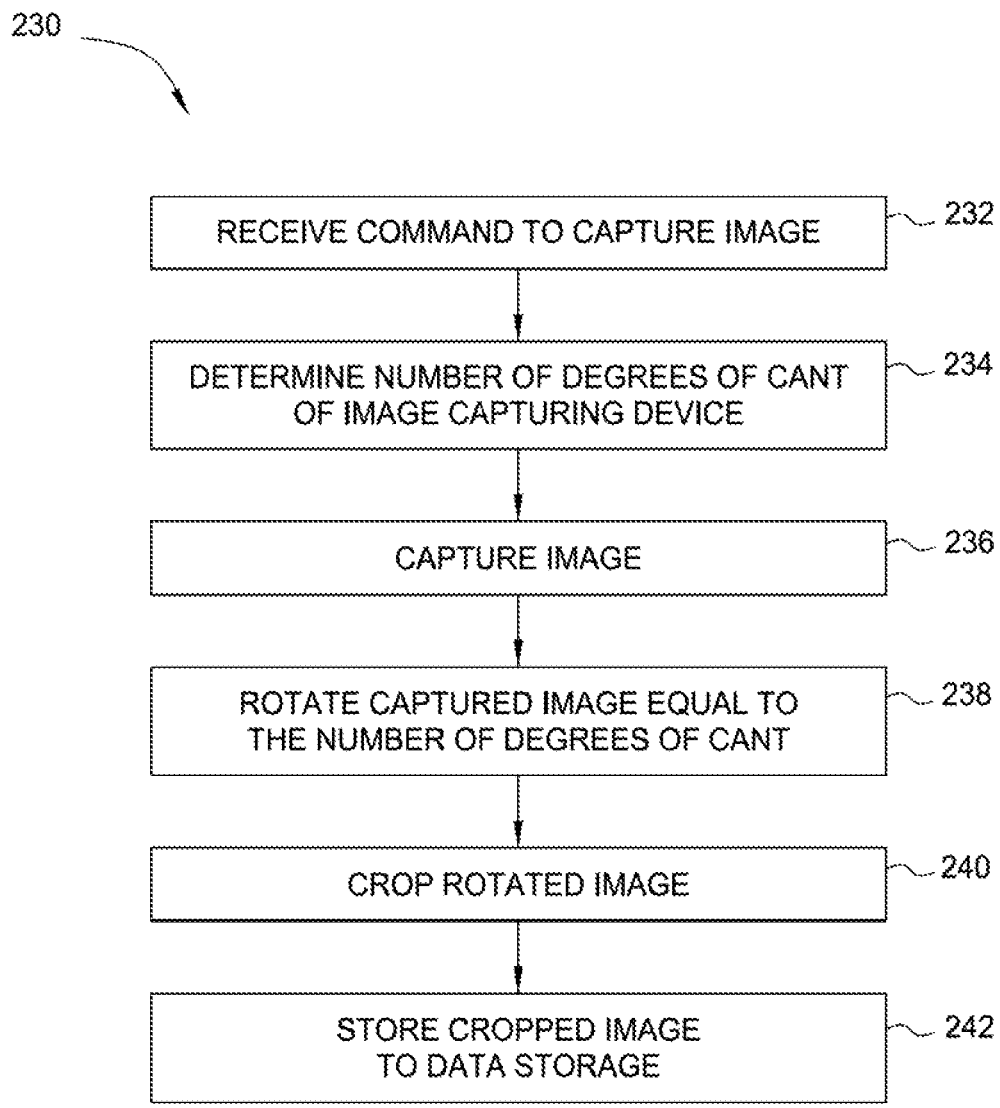
FIG. 2 is a flow diagram of a method according to one embodiment of the invention.

FIG. 2 is a flow diagram 230 of a method according to one embodiment of the invention. Flow diagram 230 begins at operation 232. In operation 232, a command is received by an image capturing device, such as system 100, to capture an image. The command may be initiated, for example, by a user of the image capturing device pressing a button, which instructs the image capturing device to capture an image.

Concurrently with or subsequent to receiving the command, in operation 234, the number of degrees of cant of the image capturing device are determined in response to the command to capture an image. The number of degrees of cant are indicative of the rotational tilt of the image capturing device with respect to vertical. The determination of the magnitude of tilt of the image capturing device is facilitated by one or more accelerometers of the image capturing device.

In operation 236, in response to receiving the command to capture an image and after having determined the magnitude of cant of the image capturing device, the image capture device captures an image. Although operation 234 is described as occurring prior to operation 236, it is contemplated that the operation 234 may occur substantially concurrently with 236. Operations 234 and 236 may occur substantially concurrently so long as the determination of the magnitude of cant is indicative of the cant of the image capturing device at the time of capturing an image.

Figure 3A:
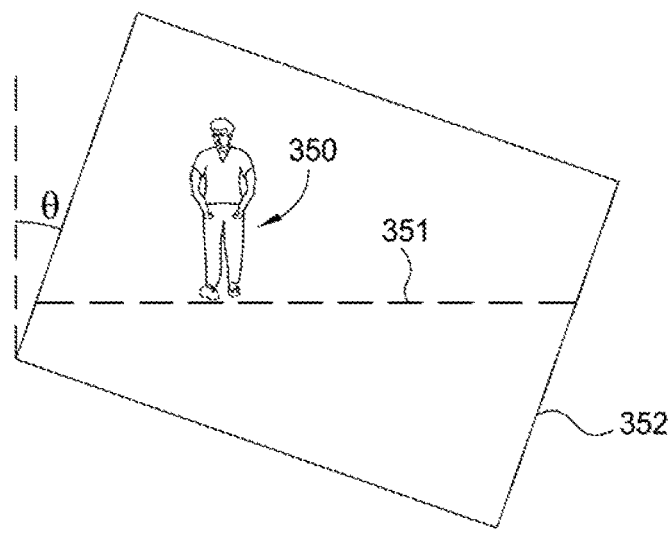
FIGS. 3A-3D illustrate the capturing, rotation, and cropping of an image according to one embodiment of the invention.
Figure 3B:
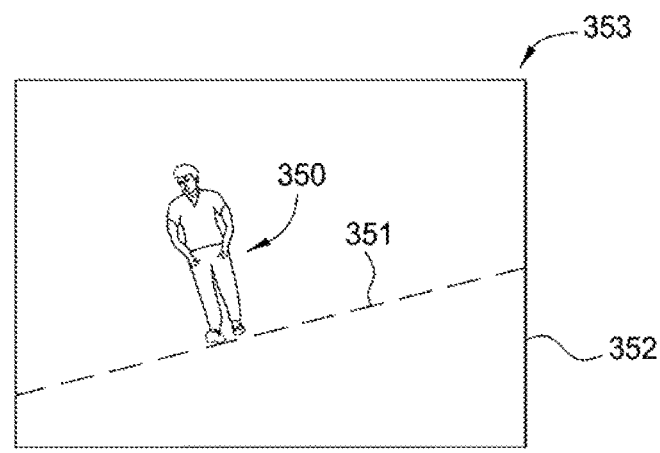

In operation 238, in response to capturing an image in operation 236, the captured image is rotated (e.g., transformed) an amount of degrees equal in magnitude to the number of degrees of cant of the image capturing device (shown in FIG. 3B). For example, if the accelerometer determines that the image capturing device is canted five degrees, the captured image is rotated five degrees. Thus, the rotated image has the appearance of being captured in a perfectly vertical orientation.

In operation 240, in response to rotating the captured image in operation 238, the rotated image is cropped. Rotation of the captured image in operation 238 properly orients the captured image, however, the frame or outline of the digital image then appears canted (as shown with respect to FIG. 3C). Cropping of the image in operation 240 sets the border of the rotated image so that the border no longer appears canted. Cropping of the rotated image is performed by fitting a bounded rectangle (e.g., a crop box) within a second bounded rectangle (e.g., the border of the rotated image). The fitting of a first bounded rectangle within a second bounded rectangle is facilitated by a software application or by the operating system. Generally, the first bounded rectangle is fit within the second bounded rectangle in order to maximize the area of the first bounded rectangle.

In operation 242, in response to cropping the rotated image, the cropped image is saved to a data storage. Thus, a captured image is rotated and cropped automatically by the image capturing device without additional input by a user. The user must only initiate the photo-capturing command, and the captured image is rotated and cropped without further user input.

FIG. 2 illustrates a flow diagram 230 of a method according to one embodiment of the invention; however, additionally embodiments are also contemplated. Optionally, both the original captured image and the cropped image may be saved to the data storage. Additionally, the cropped image may be resized to the size of the original captured image. Furthermore, the cropped image may also be displayed to a user, for example, on a display of the image capturing device.

FIGS. 3A-3D illustrate the capturing, rotating, and cropping of an image according to one embodiment of the invention. FIG. 3A illustrates an object 350 positioned on a level ground 351 as viewed through an image capturing device. The image capturing device (and consequently, the border 352 of the captured image) is canted at an angle theta while the image is captured.

Figure 3C:
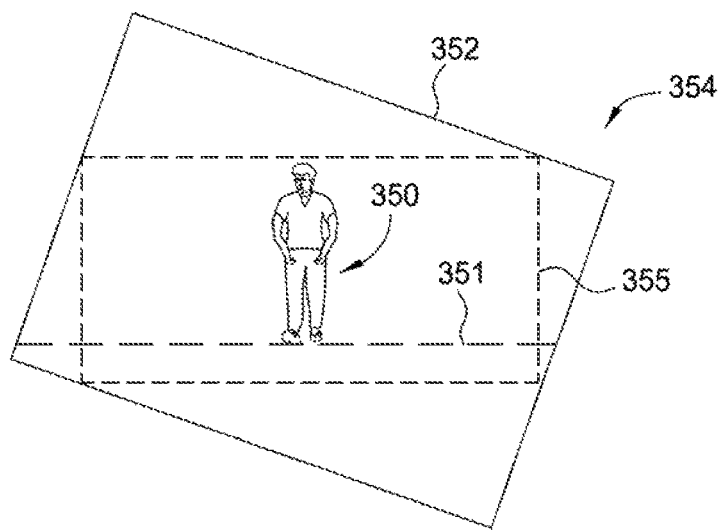

FIG. 3B illustrates a captured image 353 from FIG. 3A as the captured image 353 would appear on a display of the image capturing device or other computing device. Because the captured image 353 was captured using a canted image capturing device, the captured image 353 appears canted when shown on a level display. In order to make the object 350 and the level ground 351 appear properly oriented the captured image 353 must be rotated theta degrees, as is shown in FIG. 3C. However, rotation of the captured image 353 results in the border 352 of the captured image 353 remaining canted, as is shown by the rotated image 354. In order to display the captured image 353 in the proper orientation with borders in the proper orientation, the rotated image 354 may be cropped by fitting a first bounded rectangle 355 (e.g., a crop box) within a second bounded rectangle (e.g., border 352) of the rotated image 354. The first bounded rectangle 355 crops the rotated image 354, and thus, the first bounded rectangle 355 becomes the border of the cropped image. The first bounded rectangle 355 is oriented negative theta degrees with respect to the rotated image) in order for the border of first bounded rectangle 355 to appear without a cant.

Figure 3D:
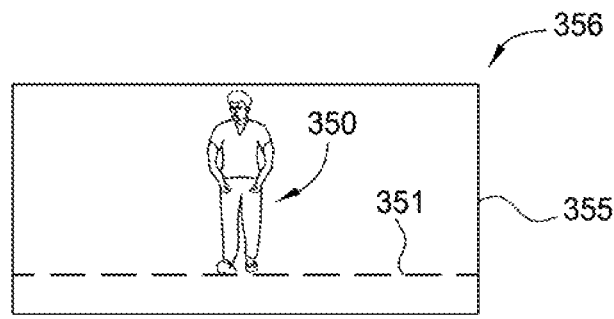

FIG. 3D illustrates a cropped image 356 having a border which is defined by the first bounded rectangle 355. It should be noted that the object 350 of the cropped image and the border of the cropped image are both properly oriented and do not give an appearance of cant. Thus, the cropped image 356 can be displayed in on a viewing device in a proper orientation, even though the image was originally captured in a canted orientation. Furthermore, the cropped image 356 is displayed in the proper orientation without user instruction; a software application performs the rotation and cropping of the canted image automatically. It is contemplated, however, that this feature may be disabled as desired by the user. It is also contemplated that the cropped image 356 may be resized automatically by the software application. Because of the high degree of quality of present image capturing devices, it is believed that most cropped images can be resized without a noticeable degradation in image quality.

Figure 4:
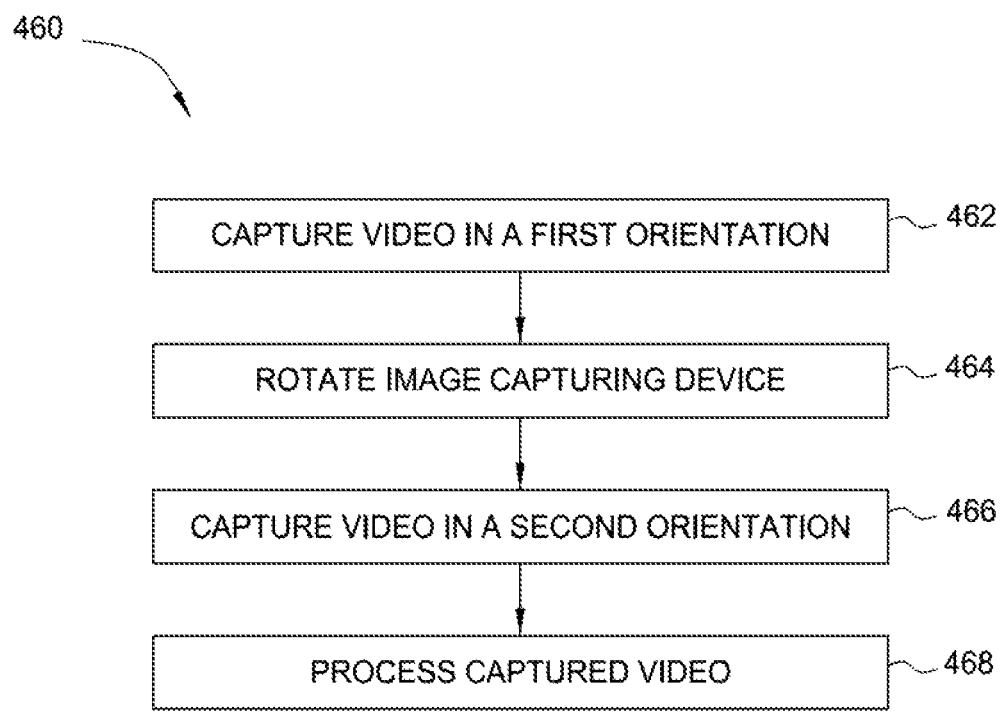
FIG. 4 is a flow diagram of a method according to another embodiment of the invention.

FIG. 4 is a flow diagram 460 of a method according to another embodiment of the invention. The flow diagram 460 illustrates a method of maintaining video orientation when capturing video with an image capturing device, such as the system 100. The method of FIG. 4 is particularly useful when the image capturing device is rotated during video capture, for example, from a portrait orientation to a landscape orientation and/or vice versa.

Flow diagram 460 begins at operation 462, in which an image capturing device captures a video in a first orientation, such as a portrait orientation. In operation 464, the image capturing device is rotated, for example, 90 degrees. The image capturing device may be rotated by a user which is supporting the image capturing device. When the image capturing device is rotated, the amount of rotation is determined by the accelerometer and saved to a data storage of the image capturing device. The accelerometer data is correlated to a corresponding time period of the video, so that the amount of rotation during image capturing is related to specific intervals in the captured video. The relationship of accelerometer data to specific time points of the captured video facilitates accurate post-capture processing of the captured video, such as rotation stabilization of the captured video, which will be further explained with respect to operation 468. It is contemplated that the image capturing device may be rotated multiple times while capturing video. After the camera has been rotated, video is captured by the image capturing device in a second orientation during operation 466.

Because of the 90 degree rotation, during operation 464, traditional videos would display a 90 degree rotation during playback. However, the image capturing device and photography application of the present invention maintain the orientation of the captured video in a single orientation, even though the video was captured in two different orientations. For example, the video may be post-capture processed by the photography application of the image capturing device during operation 468 so that the captured video appears to be in a single orientation.

Post processing of the captured video generally includes rotating the video captured in the first orientation (and the video captured during the rotational period of the image capturing device) to match the captured video in the second orientation. Thus, the orientation of the captured video at the conclusion of video capturing determines the orientation of the entire processed video for playback purposes. Because the image capturing device includes one or more accelerometers, the amount of rotation of the image capturing device, and when the rotation occurs, can be accurately determined and utilized to remove the perceived rotation of the captured image via post-capture processing.

The perceived rotation can be reduced or eliminated on a frame-by-frame basis using the rotation stabilization discussed above with respect to FIGS. 1-3C. In one embodiment, it is contemplated that rotation stabilization may not be applied until the image capturing device is rotated a certain angular distance, e.g., 15 degrees, 30 degrees, or 45 degrees, which may be selected by the user or the application developer. Thus, some rotation in the captured video may be allowed. In another embodiment, the angular distance of rotation may indicate when the video is captured in a second orientation. For example, rotation beyond 45 degrees may indicate that the image capturing device is in a second orientation. Angular rotation beyond the selected threshold may indicate when post-capture processing (e.g., operation 468) is to occur. In another embodiment, it is contemplated that the photography application stored on the image capturing device may facilitate intelligently deciding when to allow some rotation, or when to utilize rotation stabilize. For example, the photography application may determine which post-capture processing techniques to utilize based on the amount of time of each rotation (e.g., angular velocity of rotation).

In addition to removing the perceived rotation, the post-capture processing may also add black bars (vertical and/or horizontal) to portions of video captured in different orientations so that the entire captured video has the same width and/or height, thereby enhancing the playback experience for the user. The post-capture processing of the captured video and the application of black bars is further described with reference to FIGS. 5A-5C. After post-capture processing, the processed video may be stored in a data storage. The unprocessed vide may also optionally be stored, allowing a user access to both the processed and unprocessed videos.

Figure 5A:
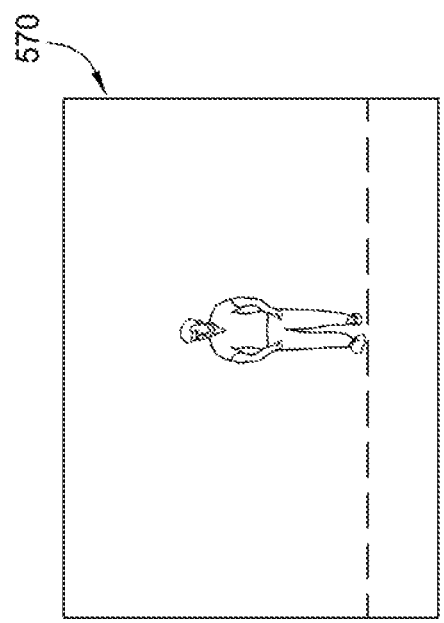
FIGS. 5A-5C illustrate video capturing according to one embodiment of the invention.
Figure 5B:
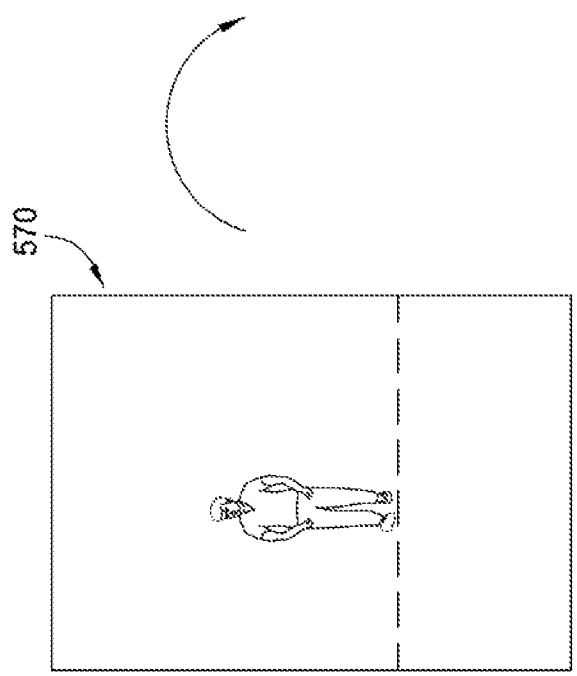
Figure 5C:
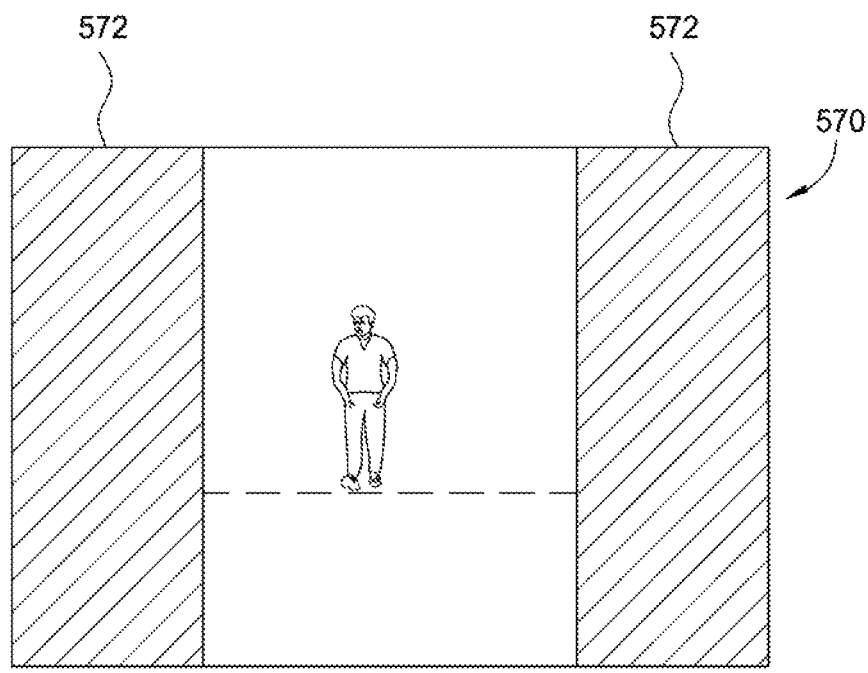

FIGS. 5A-5C illustrate video capturing according to one embodiment of the invention. In FIG. 5A, a video image 570 is captured by an image capturing device in a first orientation, for example, a portrait orientation. Subsequently, the image capturing device is rotated, and the video image 570 is captured in a second orientation, for example, a landscape orientation as shown in FIG. 5B. It is to be noted that the image capturing device can be rotated more or less than 90 degrees.

When the captured video is replayed on a display, the captured video image will exhibit a rotation during playback, due to the rotation of the image capturing device during recording. To eliminate the rotation of the captured image during playback, the video captured in the first orientation and the video captured during rotation can be rotated to match the orientation of the captured video in the second orientation (or final orientation, if multiple orientations exist). Thus, during playback of the captured video, the rotation of the image capturing device is not apparent. The rotation of the video in the first orientation is facilitated by one or more accelerometers (which indicate the orientation of the image capturing device) and a photography application stored on the image capturing device. For example, rotation stabilization which is discussed with reference to FIGS. 1-3C may be applied to eliminate the perception of rotation during video playback.

Because the captured video was recorded in multiple orientations, the dimensions of the captured video will vary through the length of the captured video. To facilitate smoother playback of the captured video, vertical "black bars" may be added to the edges of the captured video so that the video has the same width throughout the entire playback. Optionally, horizontal black bars also be added to the top and bottom of the images, as desired, to provide a uniform vertical height. FIG. 5C illustrates a video image 570 having black bars 572 covering the outer portions thereof to give the appearance of constant width of the captured video during video playback. For example, video captured in the portrait orientation (See FIG. 5A) and video captured in the landscape orientation (See FIG. 5B) are displayed with a constant width due to the black bars 572 covering portions of the video image 570 captured in the landscape orientation. Thus, as described above, video can be captured in multiple orientations, and using methods herein the video can be displayed so that the difference is orientations is not noticeable.

FIG. 4 illustrates one embodiment of capturing video; however, additional embodiments are also contemplated. In one embodiment, it is contemplated that a user may preselect the default orientation of the video. In another embodiment, the orientation may be selected during post-processing. In one example, prior to video capture, the user may select the first orientation as the orientation to maintain for the video going forward. In another embodiment, the video will record both orientations, but permit the user to select the proper orientation at the editing stage.

Figure 6A:
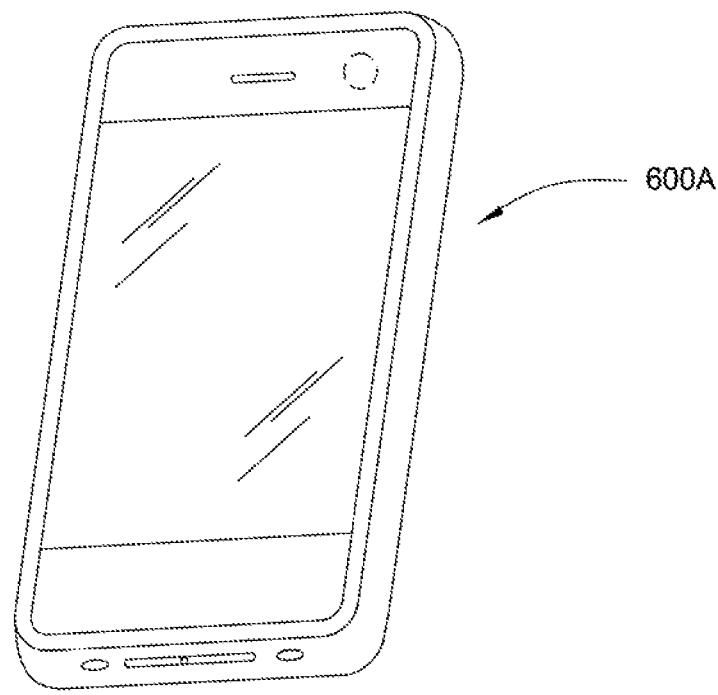
FIGS. 6A-6C illustrate exemplary systems for practicing embodiments of the invention.
Figure 6B:
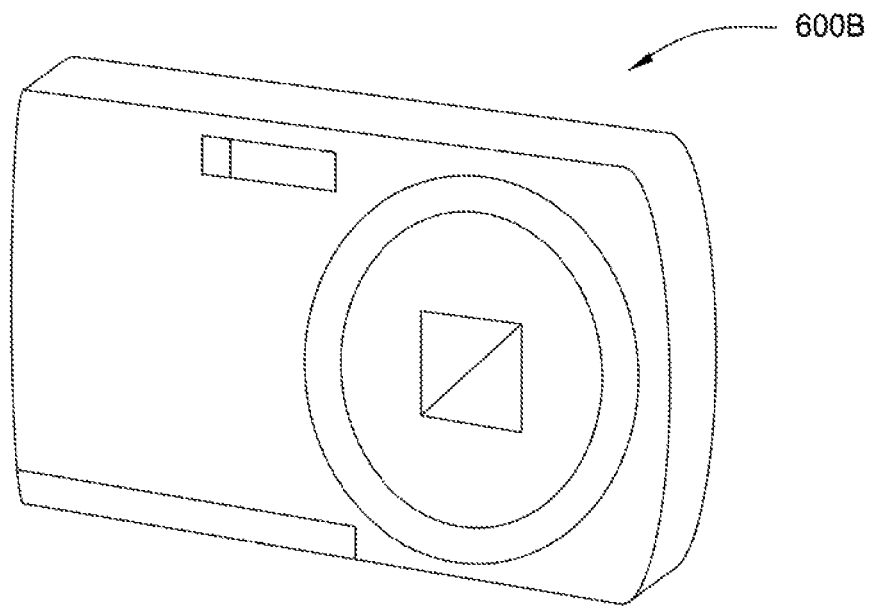
Figure 6C:
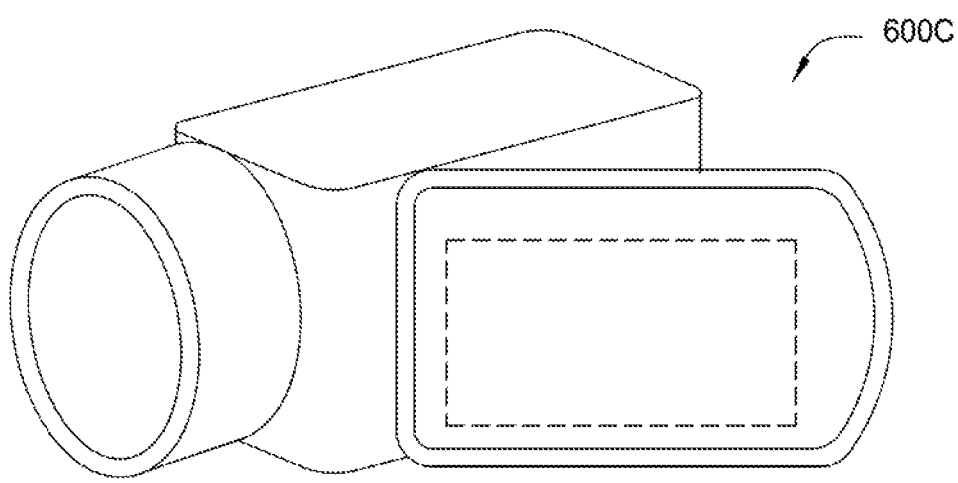

FIGS. 6A-6C illustrate exemplary systems for practicing embodiments of the invention. FIG. 6A illustrates a system 600A, such as a smart phone, in which embodiments of the invention may be practiced. The system 600A optionally includes all the components of the system 100 discussed with reference to FIG. 1. The system 600A may be utilized to rotationally stabilize images and video as described herein.

FIG. 6B illustrates a system 600B, such as a digital camera, in which embodiments of the invention may be practiced. The system 600B optionally includes all the components of the system 100 discussed with reference to FIG. 1. The system 600B may be utilized to rotationally stabilize images and video as described herein.

FIG. 6C illustrates a system 600C, such as a video camera or camcorder, in which embodiments of the invention may be practiced. The system 600B optionally includes all the components of the system 100 discussed with reference to FIG. 1. The system 600C may be utilized to rotationally stabilize images and video as described herein.

Benefits of the present invention include the elimination of cant in captured images and the elimination of video rotation by a software application at the time of capturing the image or video. The images and video are processed or edited real time by the image capturing device automatically, thereby eliminating the need to manually edit video or images after the fact. Furthermore, manual editing of images and video often requires expensive software, which is no longer necessary due to embodiments herein. Thus, embodiments described herein eliminate the need for user-performed editing to remove undesired rotation from images and video, as well as the need for expensive software required to perform the editing.

While the foregoing is directed to embodiments of the present invention, other and further embodiments of the invention may be devised without departing from the basic scope thereof, and the scope thereof is determined by the claims that follow.

We claim:
1. A method of recording video, comprising:
  receiving an instruction to capture a video with a video capture device;
  in response to receiving the instruction, capturing the video in a first orientation;

detecting a change in orientation of the video capture device from the first orientation to a second orientation different than the first orientation;

capturing the video in the second orientation;

receiving an instruction to stop capturing the video; and in response to receiving the instruction to stop capturing the video, processing the captured video, wherein processing the captured video comprises:

orienting the video captured in the first orientation to the second orientation by determining a degree of cant between the first orientation and the second orientation for each frame of the video captured during the change in orientation;

rotating each frame of the video capture by the determined degree of cant; and cropping each rotated frame.

2. The method of claim 1, further comprising adding black bars to each cropped frame so that videos captured in the first orientation have the same height or width as videos captured in the second orientation.

3. The method of claim 1, wherein the degree of cant is determined using one or more accelerometers.

4. The method of claim 3, wherein the determined degree of cant corresponding to each frame of the captured video is stored to a data storage while capturing the video in the first orientation, capturing the video in the second orientation, and capturing the video during the change in orientation.

5. The method of claim 1, further comprising storing the processed captured video to a data storage.

6. The method of claim 5, further comprising storing the video captured in the first orientation, the video captured in the second orientation, and the video captured during the change in orientation to the data storage.

7. A non-transitory computer readable medium having a sequence of instructions for recording a video, which when executed by a processing unit of a system, causes the system to:

receive an instruction to capture a video with a video capture device;

in response to receiving the instruction, capture the video in a first orientation;

detect a change in orientation of the video capture device from the first orientation to a second orientation different than the first orientation;

capture the video in the second orientation;

receive an instruction to stop capturing the video; and in response to receiving the instruction to stop capturing the video, process the captured video, wherein processing the captured video comprises:

orienting the video captured in the first orientation to the second orientation by determining a degree of cant between the first orientation and the second orientation for each frame of the video captured during the change in orientation;

rotating each frame of the video capture by the determined degree of cant; and cropping each rotated frame.

8. The non-transitory computer readable medium of claim 7, wherein the instructions further cause the system to add black bars to each cropped frame so that videos captured in the first orientation have the same height or width as videos captured in the second orientation.

9. The non-transitory computer readable medium of claim 7, wherein the degree of cant is determined using one or more accelerometers.

10. The non-transitory computer readable medium of claim 9, wherein the determined degree of cant corresponding to each frame of the captured video is stored to a data storage while capturing the video in the first orientation, capturing the video in the second orientation, and capturing the video during the change in orientation.

11. The non-transitory computer readable medium of claim 7, wherein the instruction further causes the system to store the processed captured video to a data storage.

12. The non-transitory computer readable medium of claim 11, wherein the instruction further causes the system to store the video captured in the first orientation and the video captured in the second orientation to the data storage.

13. A system, comprising:

a camera;

a processing unit;

one or more accelerometers; and a non-transitory computer readable medium having a sequence of instructions for recording a video, which when executed by a processing unit of a system, causes the system to:

receive an instruction to capture a video with the camera;

in response to receiving the instruction, capture the video in a first orientation;

detect a change in orientation of the camera from the first orientation to a second orientation different than the first orientation;

capture the video in the second orientation;

receive an instruction to stop capturing the video; and in response to receiving the instruction to stop capturing the video, process the captured video, wherein processing the captured video comprises: orienting the video captured in the first orientation to the second orientation by determining a degree of cant between the first orientation and the second orientation for each frame of the video captured during the change in orientation;

rotating each frame of the video capture by the determined degree of cant; and cropping each rotated frame.

14. The system of claim 13, wherein the instruction further causes the system to add black bars to each cropped frame so that videos captured in the first orientation and videos captured during the change in orientation have the same height or width videos captured in the second orientation.

15. The system of claim 13, wherein the degree of cant is determined using one or more accelerometers.

16. The system of claim 15, wherein the determined degree of cant corresponding to each frame of the captured video is stored to a data storage while capturing the video in the first orientation, capturing the video in the second orientation, and capturing the video during the change in orientation.

17. The system of claim 13, wherein the instruction further causes the system to store the processed captured video to a data storage.

18. The system of claim 17, wherein the instruction further causes the system to store the video captured in the first orientation, the video captured in the second orientation, and the video captured during the change in orientation to the data storage.

19. The system of claim 13, wherein the system is a smart phone.

20. The system of claim 13, wherein the system is a digital camera.

* * * * *